(12) United States Patent
Metcalf et al.

(10) Patent No.: US 12,285,760 B2
(45) Date of Patent: Apr. 29, 2025

(54) ANALYTICAL DEVICE AND REACTION CHAMBER

(71) Applicant: PROLIGHT DIAGNOSTICS AB, Lund (SE)

(72) Inventors: Ben Metcalf, Royston (GB); Steven Wakefield, Royston (GB); Neil Pollock, Royston (GB)

(73) Assignee: PROLIGHT DIAGNOSTICS AB (SE)

( * ) Notice: Subject to any disclaimer, the term of this patent is extended or adjusted under 35 U.S.C. 154(b) by 289 days.

(21) Appl. No.: 17/610,938

(22) PCT Filed: May 12, 2020

(86) PCT No.: PCT/GB2020/051157
§ 371 (c)(1),
(2) Date: Nov. 12, 2021

(87) PCT Pub. No.: WO2020/229813
PCT Pub. Date: Nov. 19, 2020

(65) Prior Publication Data
US 2022/0241788 A1 Aug. 4, 2022

(30) Foreign Application Priority Data

May 13, 2019 (GB) .................................. 1906723

(51) Int. Cl.
*B01L 3/00* (2006.01)
*G01N 33/543* (2006.01)

(52) U.S. Cl.
CPC .. *B01L 3/502761* (2013.01); *G01N 33/54326* (2013.01); *B01L 2200/0636* (2013.01); *B01L 2200/0668* (2013.01); *B01L 2300/0819* (2013.01); *B01L 2300/087* (2013.01); *B01L 2400/043* (2013.01); *B01L 2400/0478* (2013.01); *B01L 2400/0487* (2013.01); *B01L 2400/086* (2013.01)

(58) Field of Classification Search
None
See application file for complete search history.

(56) References Cited

U.S. PATENT DOCUMENTS

2009/0062828 A1* 3/2009 Marr ................ A61B 17/00234
600/12

FOREIGN PATENT DOCUMENTS

| WO | 2006121997 A2 | 11/2006 |
| WO | 2007093939 A1 | 8/2007 |
| WO | 2015075447 A1 | 5/2015 |

OTHER PUBLICATIONS

International Search Report for Application No. PCT/GB2020/051157, Dated Aug. 4, 2020, 2 pages.

* cited by examiner

*Primary Examiner* — Lyle Alexander
*Assistant Examiner* — Mickey Huang
(74) *Attorney, Agent, or Firm* — Lerner David LLP

(57) ABSTRACT

The present invention relates to an analytical device and reaction chamber therefor. Specifically it relates to a device comprising a chamber with lobes configured such that altering the lobe configuration aids in the analytical interrogation of a portion of the fluid within the chamber.

13 Claims, 9 Drawing Sheets

ANALYTICAL DEVICE AND REACTION CHAMBER

CROSS-REFERENCE TO RELATED APPLICATIONS

The present application is a national phase entry under 35 U.S.C. § 371 of International Application No. PCT/GB2020/051157, filed May 12, 2020, which claims priority from Great Britain Application No. 1906723.0, filed May 13, 2019, all of which are incorporated herein by reference.

FIELD OF INVENTION

The present invention relates to an analytical device and reaction chamber therefor. Specifically it relates to a device comprising a chamber with lobes configured such that altering the lobe configuration aids in the analytical interrogation of a portion of the fluid within the chamber.

BACKGROUND

One solution to the problem of the long turnaround that many diagnostic tests take is the development of point-of-care (PoC) testing. PoC enables faster access to diagnostic test results allowing for more rapid clinical decision making. PoC systems reduce the complex, labour-intensive, skilled diagnostic workflows traditionally carried out in central laboratories into a simple, automated reusable test instrument that can perform sample-to-answer diagnostic tests using a low-cost, self-contained, disposable testing device, for example, a cartridge or strip containing analytical elements.

Diagnostic assays are often first developed in a micro-titre plate format to allow for high-throughput experimental testing of various conditions. Developing an assay to perform well with clinical biological samples from multiple patients' presents a particular challenge because such samples can include multiple inhibitory or interfering substances which can further be different between different patient groups. This naturally leads to a substantially increased development effort as the assay must be developed against multiple different sample types to work simultaneously.

A key challenge in developing diagnostic assays for use in PoC systems is translating the initial assay development work undertaken into a format suitable for integration into a disposable test device. The limitations of such disposable test devices (for example, restrictions on the fluid manipulation steps available) often lead to systems that require significant re-development of the assay to fit within whatever test format is desired. This is often accompanied by a subsequent reduction in achievable sensitivity.

This leads to a second key challenge—achieving the required sensitivity of the diagnostic test on the disposable fluidic device. Previous systems have overcome this by trying to amplify the signal at the end, either through re-engineering of the bio-chemistry or by using additional detection mechanisms such as surface plasmon resonance (SPR) and electro-chemical detection. This can often result in deviation from previously developed assays which then require significant further development.

A third key challenge is the diagnostic test variability introduced by differences between individual biological samples. This often requires significant development to improve this response, often requiring development to be conducted on individual patient samples which can significantly increase both the development time and cost of the assay.

Current solutions include the development of a new diagnostic assay around the target format for the disposable test device. Examples of this approach include Abbott iStat, Philips Minicare, Siemens Stratus and Alere Triage. However, the development of such devices comes at a significant development cost and increases the associated development time due to the reduced experimental throughput possible by developing assays on a single-use platform. Alternatively, disposable test formats may be developed that enable the translation of an existing diagnostic assay. Examples of this approach include LSI Medience Pathfast, Biomerieux Vidas and Radiometer AQT90 FLEX. However, this approach comes with the risk that the sensitivity of the assay is compromised resulting in an inaccurate reading of the target analyte.

In prior arrangements, microfluidic devices have been suggested as a PoC compatible system, however these devices have been found to have sub-optimum mixing of reagents, leading to inadequate interaction between the reactants and resulting in a detrimental impact on the sensitivity and accuracy of such a device. Furthermore, these previous devices are unable to combine multiple fluidic functions into a single functional area, instead requiring separate functional areas to complete different tasks such as the mixing of reagents and washing steps. The latter results in the production of complex devices often requiring fundamental assay re-structuring to eliminate the requirement for one or more of these functions.

Therefore, there is a particular need in the art for an analytical device wherein the function of an individual micro-titre well can be effectively mimicked, whilst in a PoC compatible system, without significant re-development of an existing diagnostic assay. Additionally, there is a need for an analytical device which can improve the interaction between reactants and enable the control of fluid movement to aid in analytical interrogation. The present invention seeks to meet these needs and also provides an analytical device in which a central reaction chamber can be altered to change its configuration, thus overcoming the aforementioned of issues of sensitivity and accuracy of prior art systems.

SUMMARY OF THE INVENTION

The present invention provides an analytical device comprising a first chamber, wherein the first chamber comprises lobes structured such that altering the lobe configuration aids fluid movement around said first chamber such that an analytical interrogation of a portion of the fluid can be performed.

The present invention further provides for the use of such an analytical device in the context of an immunoassay, particularly a magnetic-bead based immunoassay.

The present invention further provides for the use of an arrangement of plungers and magnets to alter the configuration of the lobes within the chamber and to aid the movement of fluid around the chamber.

The present invention further provides for an analytical device with an additional second and/or third chamber to improve the noise to signal ratio and allow for optical interrogation of the sample.

It will be appreciated that the present invention provides a simple analytical device which is flexible in use and which can provide improved accuracy and sensitivity when compared to prior art systems.

DESCRIPTION OF FIGURES

The invention will now be described with reference to the accompanying figures, in which.

DETAILED DESCRIPTION

The present invention provides for an analytical device which can effectively mimic the function of an individual micro-titre well, allowing an analytical assay previously developed on such a format to be more easily translated onto this platform.

As shown in the figures, and described in more detail below, the present invention provides for an analytical device comprising a first chamber, wherein the first chamber comprises lobes structured such that altering the lobe configuration aids fluid movement around said first chamber such that an analytical interrogation of a portion of the fluid can be performed.

The chamber is where all relevant reactions take place (formation of immuno-complexes, washing of immuno-complexes and detection of immune-complexes); in order to best mimic the function of an individual micro-titre well, the general structure of the analytical device is built around this central reaction chamber.

The present invention provides a design of a central reaction chamber that can both generate effective turbulence for the mixing of reagents, and in the same chamber, still permit good laminar flow to allow for an effective exchange of fluid when required.

The lobes are two distinct compartments connected by a neck, so that fluid in one of the lobes can pass to the other unobstructed.

The analytical interrogation can be any technique in which the concentration of a particular substance within a sample may be determined.

The fluid for analytical interrogation may be a biological sample, for example, a blood sample, urine sample, sweat sample or spinal fluid sample which may contain a target analyte of interest. The target analyte of interest may be a protein, a RNA molecule or a DNA molecule.

The analytical device may be arranged for use in an immunoassay, a biochemical test that measures the presence/concentration of a target analyte within a sample through the use of an antibody or antigen. Immunoassays work on the basic principle of the antibody binding specifically to a target of interest and subsequently detecting the immuno-complex with a detection substrate. This detection substrate may result in, for example, a change in fluorescence.

The analytical device may be arranged for use in a magnetic-bead based immunoassay. In this particular type of immunoassay, the antibody used to specifically bind to the target analyte is immobilised on the activated surface of the magnetic particle. The magnetic particle itself contains nanoparticles of superparamagnetic magnetite embedded within a polymer matrix. This approach has a number of advantages; there is little magnetic material in the majority of biological samples which could interfere with the measurement outcome and external magnets aid in both the collection of the target analyte and the mixing of reagents.

Figure 1:
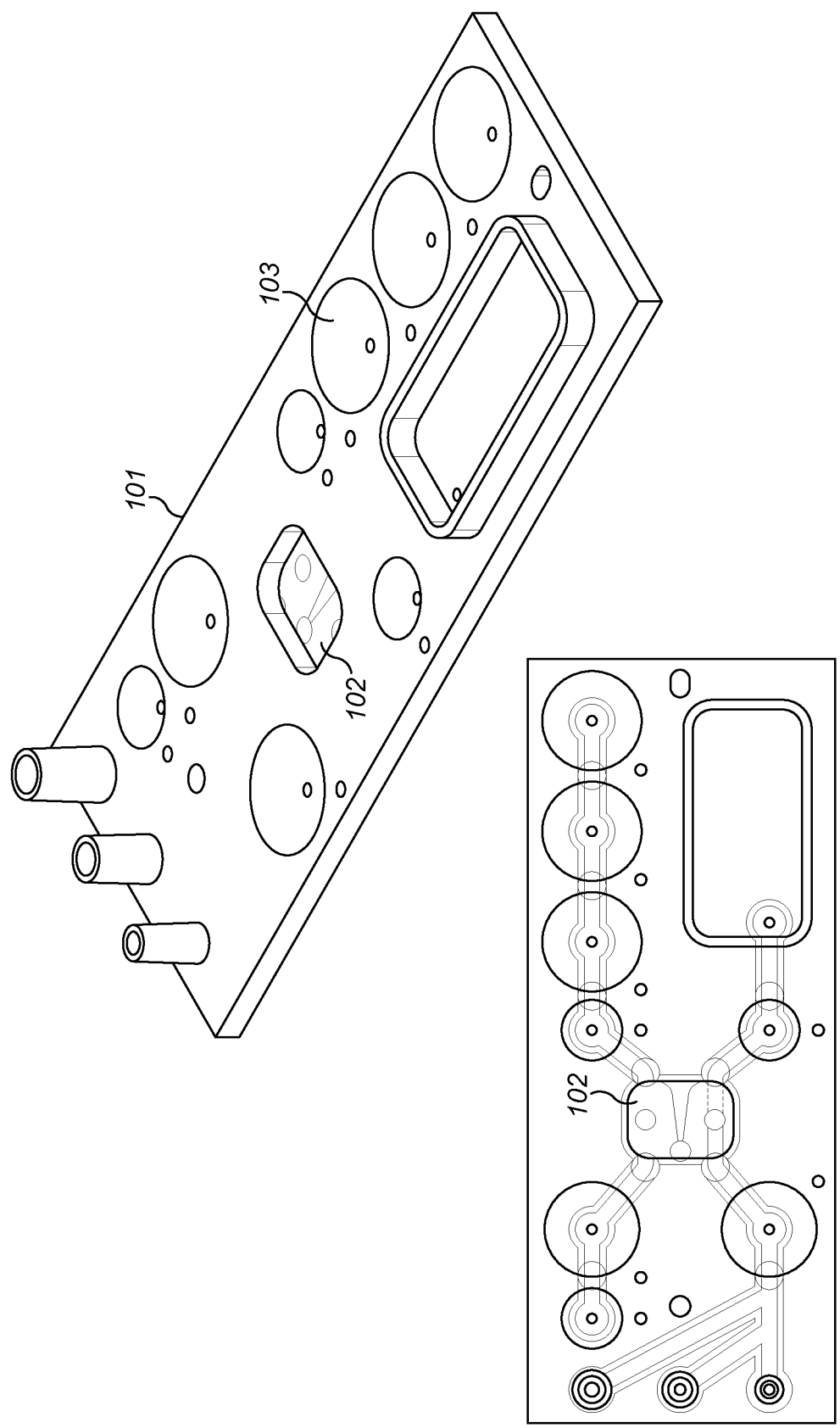
FIG. 1 shows the general structure of a fluidic device according to the invention built around a central reaction chamber.

An example of a device according to the invention is depicted in FIG. 1. The analytical device has a first chamber 102 in which immune-complexes may be formed, washed and detected. The analytical device may also comprise a store of additional wash fluids 103 arranged in such a way on the analytical device that the reactants within the first chamber 102 can be washed efficiently.

The first chamber 102 may be elongate. This elongated shape of the chamber 102 is to allow for better laminar flow within the chamber itself, therefore improving the robustness and accuracy of the assay.

Figure 3:
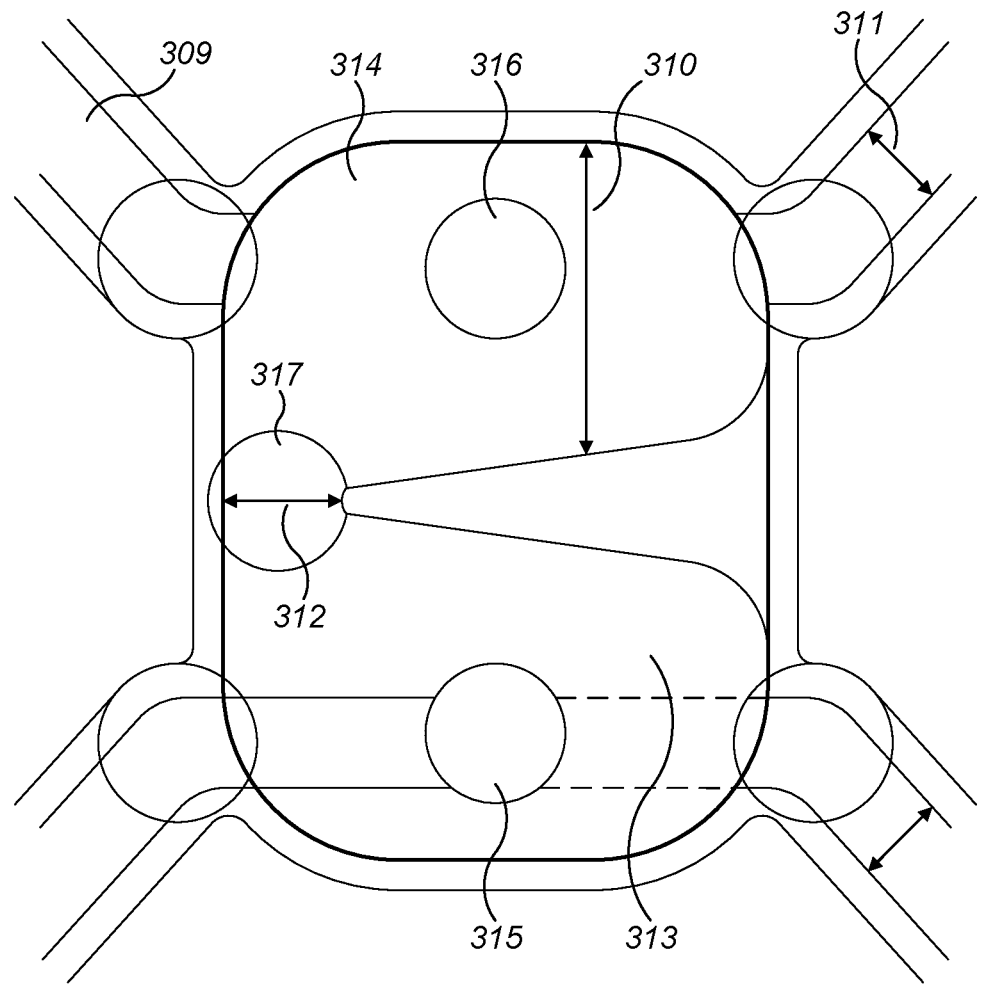
FIG. 3 shows a central reaction chamber which can be used in the invention and including magnets and plungers.

As can be seen in FIG. 3, a plurality of fluidic channels 309 connect to the chamber 102 allowing reagents to be introduced and flow through the chamber 102. In this example the total volume that the chamber 102 may accommodate is 200 µL, however reactions may take place in a volume of 20 µL, 50 µL, 100 µL, 150 µL, 300µ or 500 µL. The chamber has at least two lobes 313, 314 connected by a neck 312. These features may be defined by a flexible membrane positioned above a rigid planar base, and the membrane may be at least partially optically transparent.

Preferably the central chamber 102 should not be greater in maximum width 310 than approximately 3× the width of the channel 311 feeding into the central chamber to preserve this laminar-like behaviour. For example, the chamber 102 may be elongate along the direction of fluid flow to create a rounded rectangular shape. The fluid inlet channels 311 may be arranged into the side of the central reaction chamber 102 as shown. This is to ensure that the fluid flow remains laminar as it enters the chamber. Fluidic channels 311 entering from the 'top' or 'bottom' of the chamber 102 would experience a large increase in effective channel width causing loss of laminar flow and poor washing.

The analytical device may comprise one or more channels which comprise multiple elastomeric layers positioned within a chassis and configured such that fluid movement may be possible under both positive and negative pressure.

Figure 2:
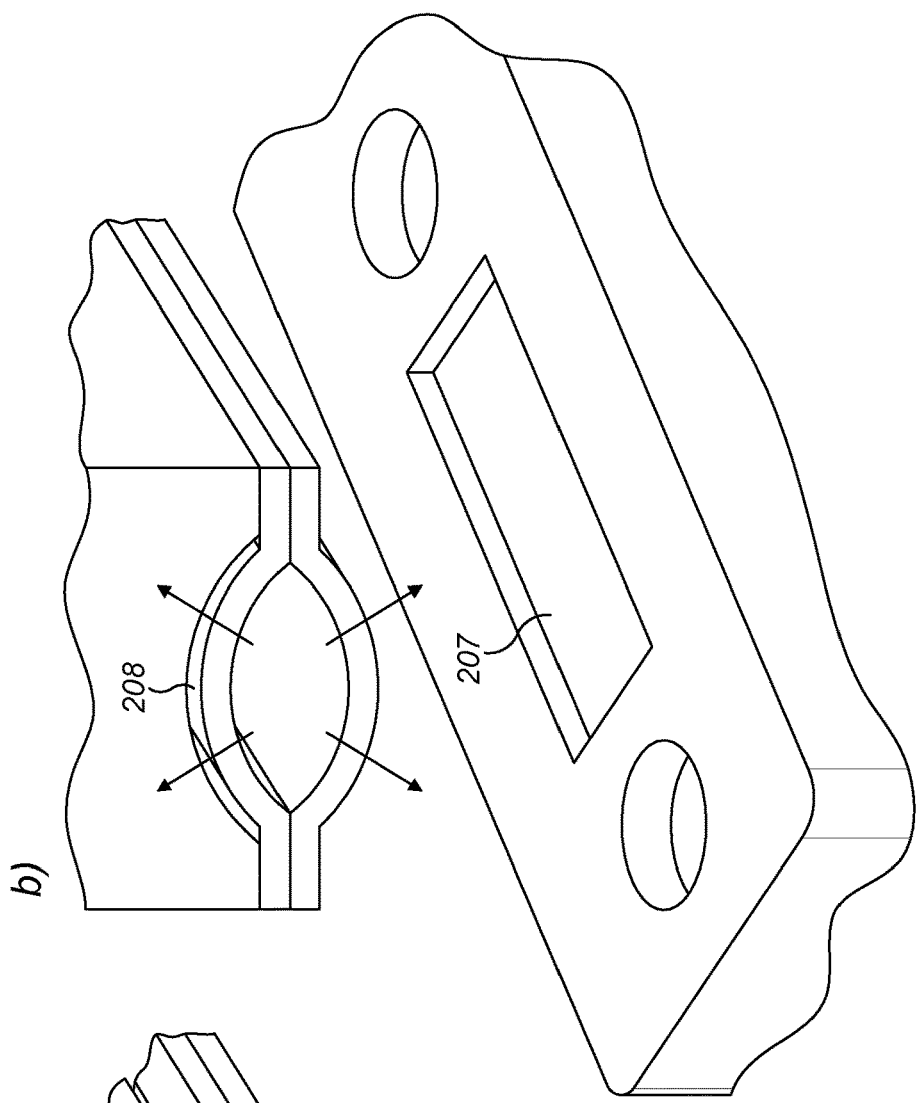
FIG. 2 shows elastomeric membranes to create fluidic channels to allow movement of fluid under both positive and negative pressure in a device according to the invention.
Figure 2:
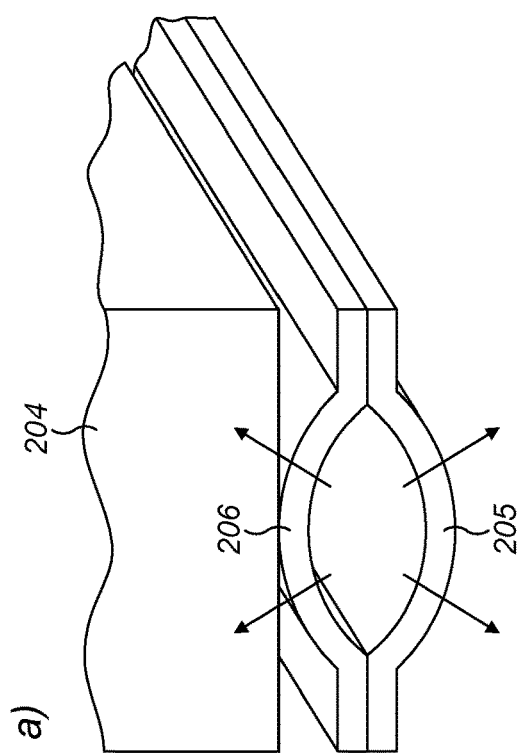

To achieve this, the device may include a modification of the fluidic channels already known in the art. Prior art arrangements use two elastomeric membranes to create a fluid channel with almost no dead volume and require the positive pressure of fluid moving through the channels to open them up. If instead it is desired to pull fluid through these channels under negative pressure, for example through aspiration by a syringe, it is necessary to modify the construction of these fluid channels to prevent them sealing closed under negative pressure. An example of such a modification is shown in FIG. 2. As part of the present invention, the second elastomeric membrane 206 is first pre-formed along the geometry of the fluid channel which creates a 'normally open' fluid channel once sealed to the first membrane 205. A channel in both the chassis 208 and the device holder 207 allows for the two membrane layers 205,206 to be pre-formed to create a normally open fluid and allows for fluid to move under both positive and negative pressure. This increases the functionality of the device by allowing a syringe to move fluid through the device through aspiration as well as through positive displacement.

At least one plunger (not shown) is positioned above the chamber 102. Plungers arranged mechanically above the central reaction chamber 102 can be controlled to squeeze one of the lobes 313, 314 of the chamber 102 making up the reaction chamber, thus forcing fluid through the neck 312 into the other lobe. This action can help drag magnetic particles through the fluid and over a magnet, or magnets, positioned underneath the chamber 317. The speed and distance with which the plunger moves to compress the lobe 313 of the reaction chamber 102 will determine the speed of the fluid flow and thus the drag force experienced by the suspended magnetic particles. The plunger speed and distance of movement of the plunger, when in use, is controlled by a stepper motor (not shown).

By controlling both the speed and the distance the plunger moves, the force exerted on the suspended magnetic particles can be made sufficient to move them from the edges of the chamber over the magnet but not sufficient to pull them away from the magnet once they are closer to the magnet.

Additionally, the plungers can be arranged such that the mixing of reactants is increased compared to if no plungers were present. This is advantageous in many applications as the incubation time required for the analyte to form ELISA sandwich complexes within the reaction chamber is limited by the diffusion rate of the large molecules through the reaction volume.

The analytical device comprises at least one magnet positioned on one side of the first chamber 102. The magnet may be positioned such that it corresponds to the mid-point of the lobes 313, 314 within the first chamber 102 and/or the connecting neck 312 of the lobes. Additionally or alternatively the analytical device can have at least one magnet 312, 315, 316 configured such that it can alternate from an inactive position to an active position.

Further magnets can be added to the reaction chamber to accomplish collection of magnetic particles in stages. For example, for large chambers, the force required to drag particles from the edges of the chamber may be so great that it overcomes the magnetic force available and the particles never become collected. Instead, additional magnets 315, 316 can be placed around the chamber. For example, these could be in the centre of each lobe 313, 314 of the chamber 102 as well as in the neck 312 between the two lobes 313, 314.

Figure 4:
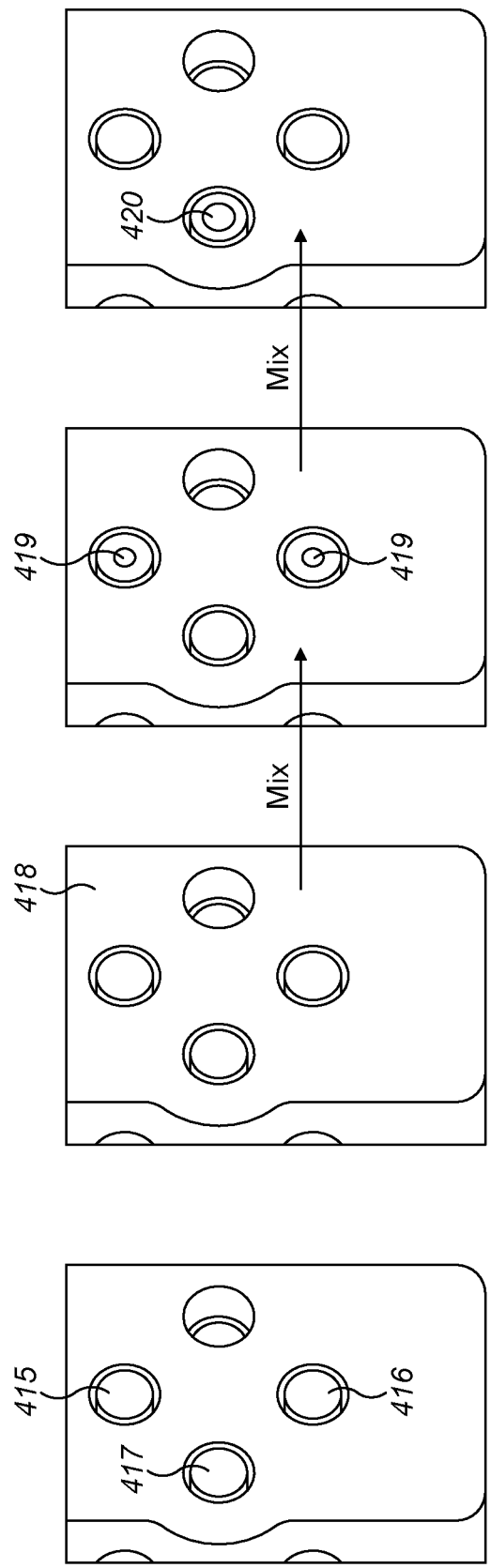
FIG. 4 shows the positioning of magnets and alteration of their activation states within the central reaction chamber to collect the magnetic particles in one location.

FIG. 4 shows the operation of magnets in the present invention. FIG. 4A shows the permanent magnet with the presence of two additional magnets to the side, all of which are individually controlled. FIG. 4B shows the configuration of the magnets with the side magnets 'up'. FIG. 4C shows when the side magnets are 'up' the magnetic beads from the edge of the chamber collect onto the side magnets. FIG. 4D shows when the centre magnet is 'up' and the side magnets are not; all magnetic beads may now be collected on the centre magnet in the neck of the first chamber.

These additional magnets reduce the required force from the plunger to capture magnetic particles from the edges of the chamber 419. By subsequently removing these magnets and raising the centre magnet all of the magnetic particles may be gathered in a single position 420. A similar protocol could be extended for larger chambers using further magnets to collect the magnetic particles from all areas of the chamber in stages and then bring them all to one central location by selecting which magnets are raised or active and using the plungers to agitate the reaction chamber with a controlled force.

Figure 5:
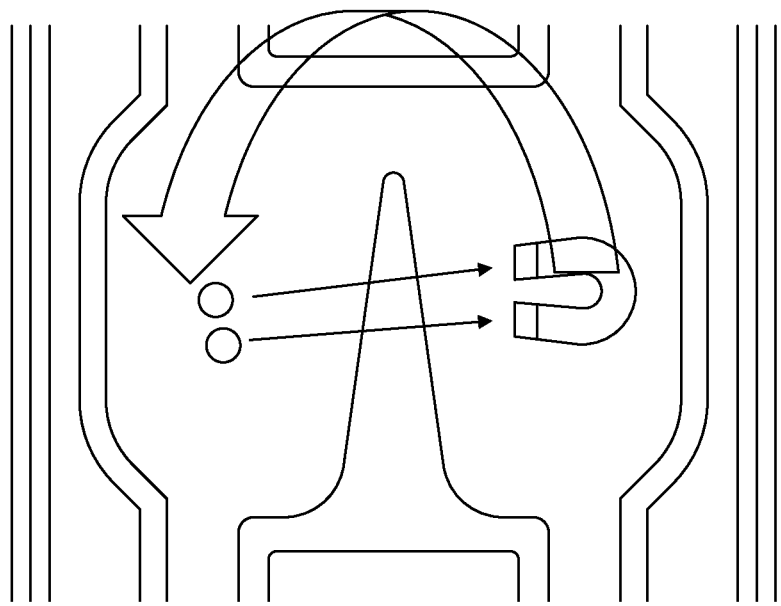
FIG. 5 shows the positioning of magnets to improve the mixing of reactants when magnetic particles are present during operation of the invention.
Figure 5:
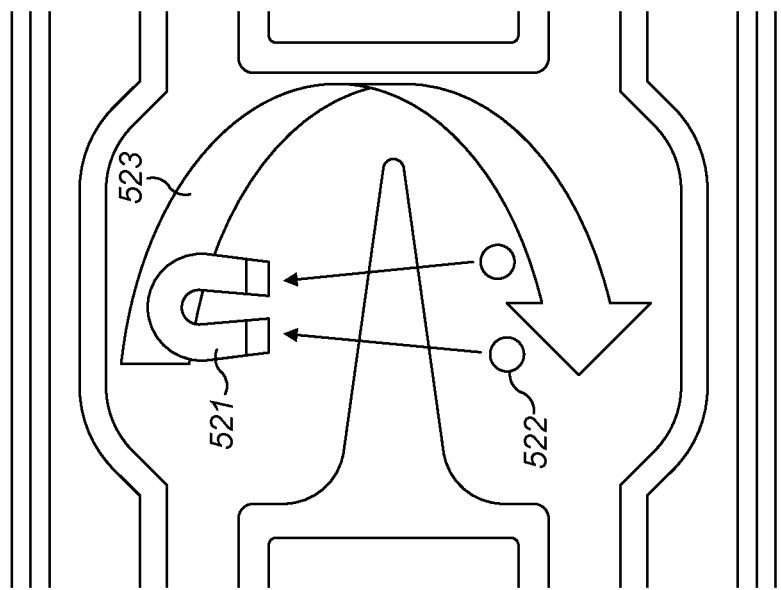

The use of magnets in the present invention provides a method to further improve this mixing when the reactants contain suspended magnetic particles. FIG. 5 shows a magnetic field 521 placed under an upper lobe of the reaction chamber will attract magnetic particles 522 toward it. At the same time, a plunger can compress the upper lobe to force fluid toward a lower lobe 523. This creates an opposing motion of the bulk fluid flow and the suspended magnetic particles thereby effectively exchanging the fluid immediately surrounding the magnetic particles and increasing the volume of liquid each particle is exposed to. With this method it is possible to further reduce the time required for effective mixing of all reactants in the chamber.

Figure 6:
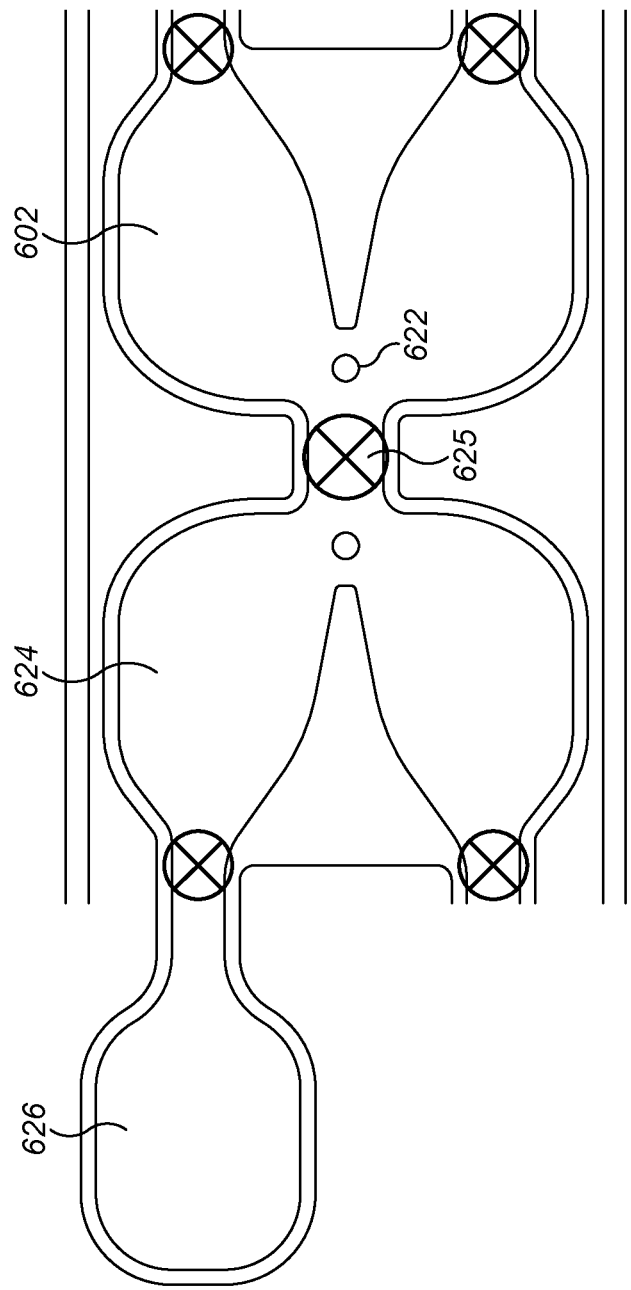
FIG. 6 shows the optional addition of a second and third chamber to the first central reaction chamber of the invention.

Referring to FIG. 6, the analytical device can comprise a second chamber 624 directly linked to the first chamber 602, linked by a connecting channel. Such an arrangement allows the contents of the reaction chamber, including any suspended magnetic particles 622 to be transferred to the second chamber 624. This second chamber 624 may be used to improve the signal to noise of the assay by providing a clean space, not contaminated with other substances, such as a detection enzyme, for the beads to reside prior to the analytical interrogation of the sample.

The analytical device can further comprise a third chamber 626 directly linked to the second chamber 624, again linked by a connecting channel. Preferably, the third chamber 626 may be configured to allow for optical interrogation of its contents.

Figure 7:
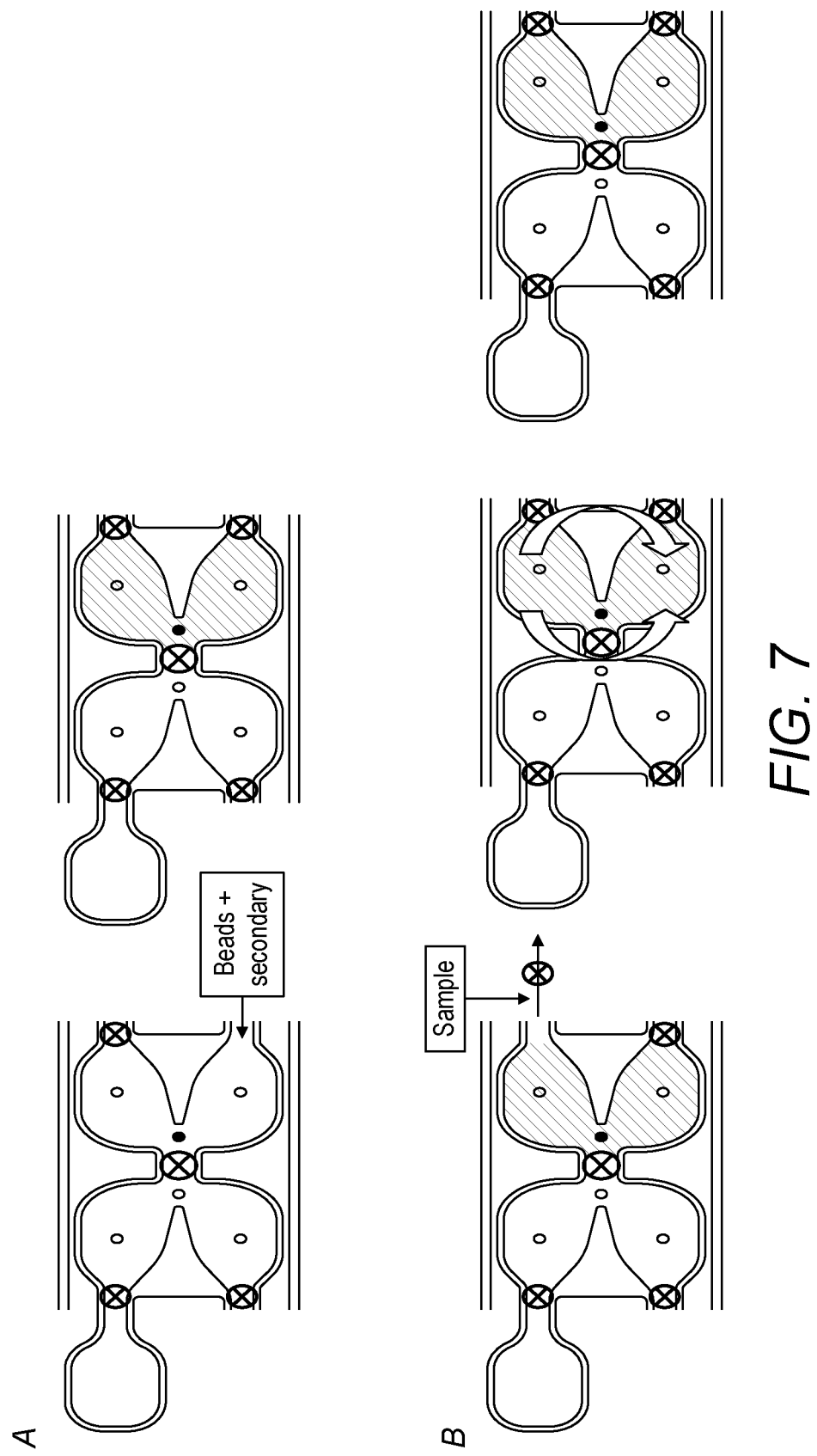
FIG. 7 shows the process by which fluid may be transferred from one chamber to the next to enable easier analytical interrogation.
Figure 7:
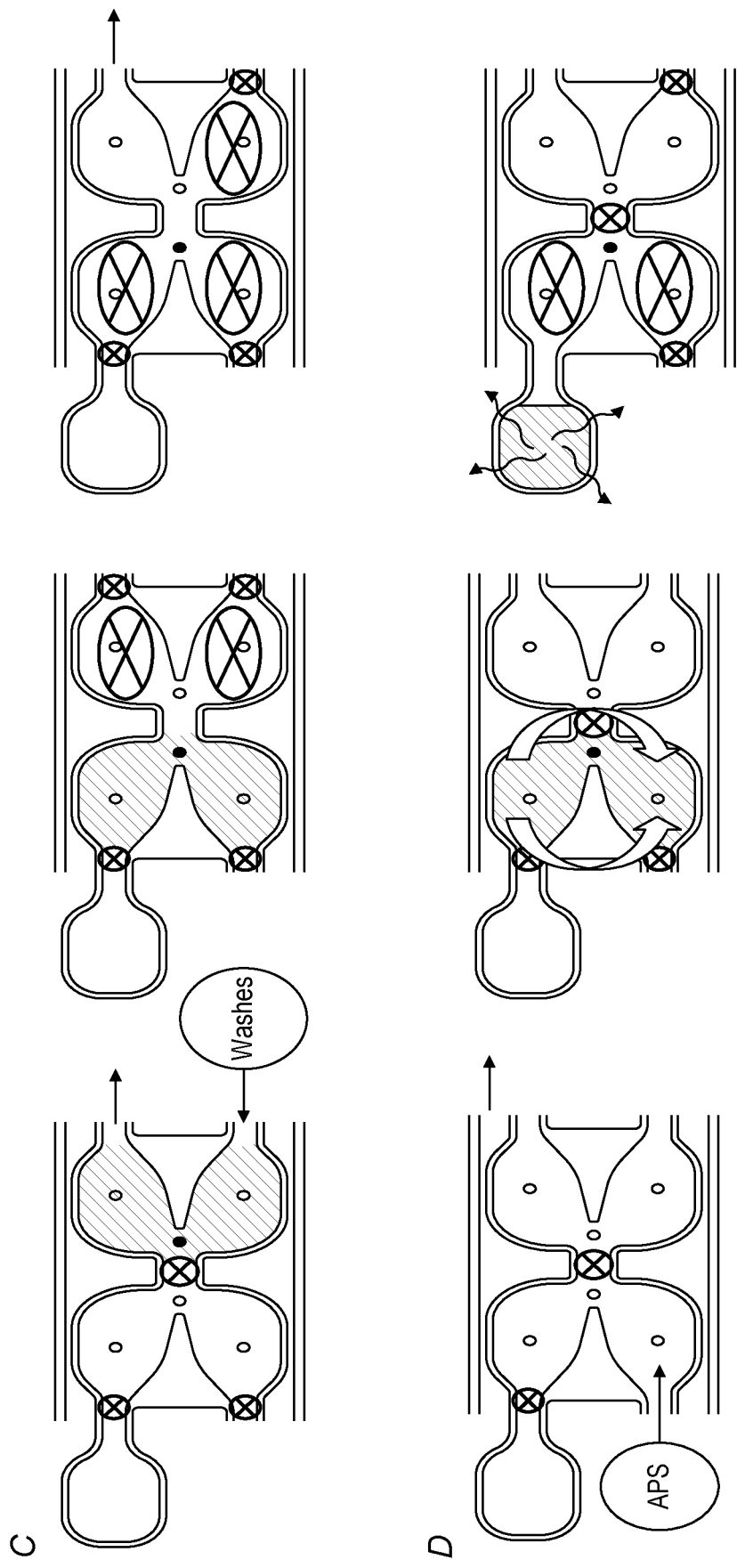

The addition of a third chamber 626 allows for the final reactants to be moved to a location on the device whereby optical interrogation is easier. For example, the device may be configured such that the area directly above and below the second reaction chamber 624 is obstructed with mechanical actuators, making optical interrogation of the second reaction chamber 624 more difficult. Therefore, the creation of a third chamber 626, lacking the mechanical actuators, allows for easier access to the portion of the fluid to be analysed. The manner in which fluid may be moved through subsequent chambers is depicted in FIG. 7. The process includes the following steps: A) Adding the reagents and priming, B) adding the sample and incubating the sample with the already present reactants, C) washing and transferring the beads to a clean mixing chamber and finally, D) adding a chemiluminescent substrate, for example, Lumigen APS-5, and moving to a clean read chamber.

Figure 8:
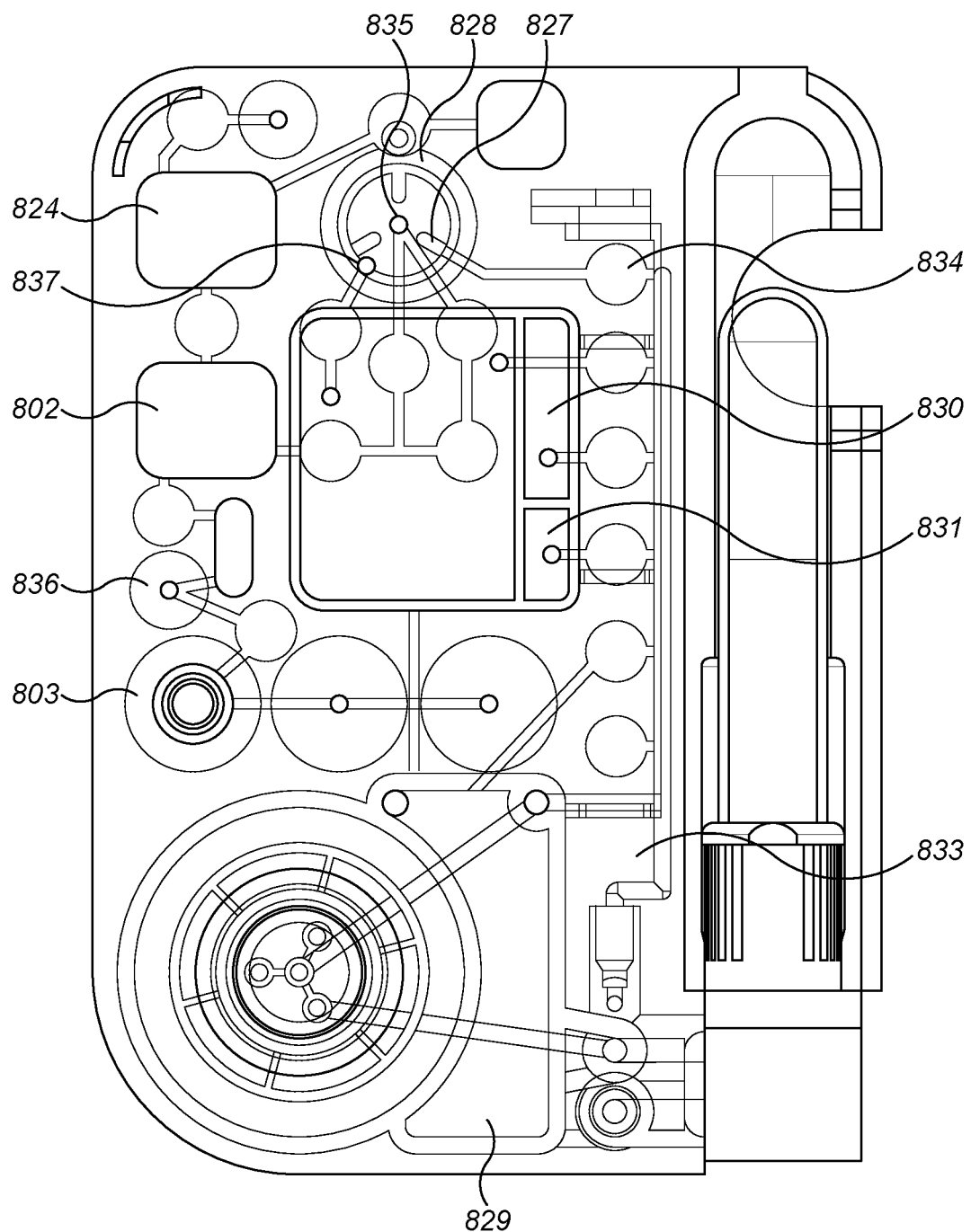
FIG. 8 shows an analytical device according to the invention featuring a first, second and third reaction chamber.

An analytical device comprising all three chambers, as described above is depicted in FIG. 8. This device may also comprise an apparatus appropriate for isolating a target analyte of interest 828 which can then be directed to the central reaction chamber 802. The device may also have fluid pots for storing the dilution buffer 829, wash buffer 803, elution buffer 831 and a means for collecting waste 832. A syringe 833 and selectively activating valves 834 also located on the device enables the movement of different fluids around the device along the fluidic channels previously described. The device also allows for the storage of dried reagents 836 in blisters which can be sealed, for example, by foil.

As will be appreciated from the above, the present invention enables the provision of an analytical device which has a simple construction but which is capable of performing complex assays with high levels of sensitivity and accuracy.

The invention claimed is:

1. An analytical device comprising a first chamber, wherein the first chamber comprises a two-lobed structure, wherein each lobe of the two-lobed structure is connected by a neck, and the two-lobed structure is configured such that altering a configuration of the two-lobed structure aids movement of a fluid around the first chamber and an analytical interrogation of a portion of the fluid can be performed, and wherein at least one magnet is positioned within the first chamber.

2. The analytical device of claim 1, which is arranged for use in an immunoassay.

3. The analytical device of claim 1, which is arranged for use in a magnetic-bead based immunoassay.

4. The analytical device of claim 1, further comprising at least one connecting channel defined by multiple elastomeric layers positioned within a chassis and configured such that the movement of the fluid can be performed throughout the analytical device under both a positive and a negative pressure.

5. The analytical device of claim 1, wherein the first chamber is elongate.

6. The analytical device of claim 1, further comprising at least one plunger positioned above the first chamber.

7. The analytical device of claim 6, wherein a speed and a distance of movement of the at least one plunger when in use is controlled by a stepper motor.

8. The analytical device of claim 1, wherein the at least one magnet is positioned on one side of the first chamber.

9. The analytical device of claim 8, wherein the at least one magnet is configured such that it can alternate from an inactive position to an active position.

10. The analytical device of claim 8, wherein the at least one magnet is positioned at a mid-point of one lobe of the two-lobed structure within the first chamber and/or a mid-point of the neck by which each lobe of the two-lobed structure is connected.

11. The analytical device of claim 1, further comprising a second chamber directly linked to the first chamber.

12. The analytical device of claim 11, further comprising a third chamber directly linked to the second chamber.

13. The analytical device of claim 12, wherein the third chamber is configured to allow optical interrogation of its contents.

* * * * *